United States Patent [19]

Birner et al.

[11] 4,246,777

[45] Jan. 27, 1981

[54] TEST DEVICE FOR CONTAINERS

[75] Inventors: Richard A. Birner; Arthur C. Einfalt, both of Toledo, Ohio

[73] Assignee: Owens-Illinois, Inc., Toledo, Ohio

[21] Appl. No.: 63,892

[22] Filed: Aug. 3, 1979

[51] Int. Cl.³ .............................................. G01N 3/48
[52] U.S. Cl. ........................................ 73/83; 73/821
[58] Field of Search ................ 73/83, 81, 821; 100/99

[56] References Cited

U.S. PATENT DOCUMENTS

| | | | |
|---|---|---|---|
| 2,685,197 | 8/1954 | Mennesson | 73/81 |
| 3,438,250 | 4/1969 | Boutron | 73/83 X |
| 3,464,260 | 9/1969 | Heyman | 73/821 X |
| 3,470,737 | 10/1969 | Fridley | 73/81 |
| 4,061,020 | 12/1977 | Fridley et al. | 73/83 X |
| 4,159,640 | 7/1979 | Lévéque et al. | 73/81 |

*Primary Examiner*—Gerald Goldberg
*Assistant Examiner*—Joseph W. Roskos
*Attorney, Agent, or Firm*—David R. Birchall; Myron E. Click; David H. Wilson

[57] ABSTRACT

A machine for testing a container such as a paper or plastic cup. The cup rests upon a platform and its stiffness is measured by applying a given load to the side of the cup by means of a motor driven load applying arm. The applied load and the resulting deflection are determined by the direct coupling together of the cores of a force cell and a linear variable displacement transformer. The load applying arm and the coil of the linear variable displacement transformer are coupled together to compensate for an initial preload condition. The ultimate load for the predetermined deflection is monitored by a force cell and the electrical signal thus generated is converted to a direct reading digitally displaced valve.

A method for testing a cup-like container by supporting the container on a set of rollers and applying a first small force normal to the side of the container. A second greater force is applied to the side of the container until a preselected overall deflection of the container side is attained. The force existing after the container has deflected the preselected amount is converted to an electrical signal which is displayed as grams on a digital meter.

20 Claims, 12 Drawing Figures

TEST DEVICE FOR CONTAINERS

BACKGROUND OF THE INVENTION

In the manufacture of containers such as disposable drinking cups, it is necessary to determine the strength of the containers at frequent intervals so that a uniform product can be maintained. To have a quality product there must be a fair degree of uniformity between not only the individual containers manufactured on a given line but also there must be uniformity between different production lines and even different production plants located remote from one another. Heretofore the testing of containers, such as cups manufactured of paper or more recently foamed plastic sheet stock and injection molded plastic techniques, has resulted in a wide variation of test values obtained on seemingly identical cups. Part of the problem was attributable to manner in which the cup was held or positioned by the test operator. Then too, the conversion of the deflections obtained as a result of applying a given load to a cup were subject to variations and even error. The inconsistencies found in the prior art cup testing apparatus and techniques were determined to be inadequate since it was difficult to obtain the same test values when test loads were applied by different operators and at different times.

The prior art test devices required highly trained personnel to operate the test equipment and to interpret the results thus obtained.

SUMMARY OF THE INVENTION

This invention relates to the testing of containers. More particularly, the invention relates to an apparatus for the nondestructive testing of containers such as disposable drinking cups. The present invention employs a test apparatus that applies a load to the rim or sidewall area of the cup much similar to the load encountered by the cup when it is grasped by the human hand.

The apparatus provides an accurate and reliable means of applying a given deflection to the cup sidewall and converting the resulting load directly into an electronic signal that is displayed digitally.

Containers such as cups are loaded into the test apparatus by placing them one by one in an upright position on an elevator. The elevator and associated sensors then position the cup in the proper position for the application of a test load or force. The cup is then grasped by the rim or the sidewall by two or more opposing arms.

A preload is applied to the cup in a generally diametrically direction. After the initial preload application, the main test deflection is applied and the resulting load, for the predetermined inward movement, is sensed and converted to an easily readable number.

The amount of the preload placed on the side of the cup is determined by the use of a force cell. The same force cell is also utilized to ascertain the amount of the ultimate load applied when the test reading is taken. The deflection undergone by the cup sidewall is measured through the use of a linear variable displacement transducer. The core of the linear variable displacement transducer is directly coupled to the core of the load cell or force transducer to minimize any error in obtaining a direct reading of the deflection that takes place when a load is applied to the cup sidewall.

It is an object of the present invention to provide a device for measuring the stiffness of a container such as a cup.

Another object of the present invention is to provide a test apparatus that independently grasps, tests and displays a test value without manipulative steps being performed by a test operator.

An additional object of this invention is to set forth a device that gives accurate test results over a wide range of container sizes, configurations and materials from which the container is manufactured.

A further object of the present invention is to provide a grasping means for either applying a load to the rim of the container or to the sidewall of the container.

Another object of this invention is to provide a method of applying a deformation to the exterior of a container and recording the insuing test load in terms of a force.

Still another object of the invention is to provide a method of testing a container without human intervention during the test cycle.

Additional objects and advantages of the present invention can be readily understood by reference to the following specification drawings and claims.

DESCRIPTION OF THE PREFERRED EMBODIMENT

Figure 1:
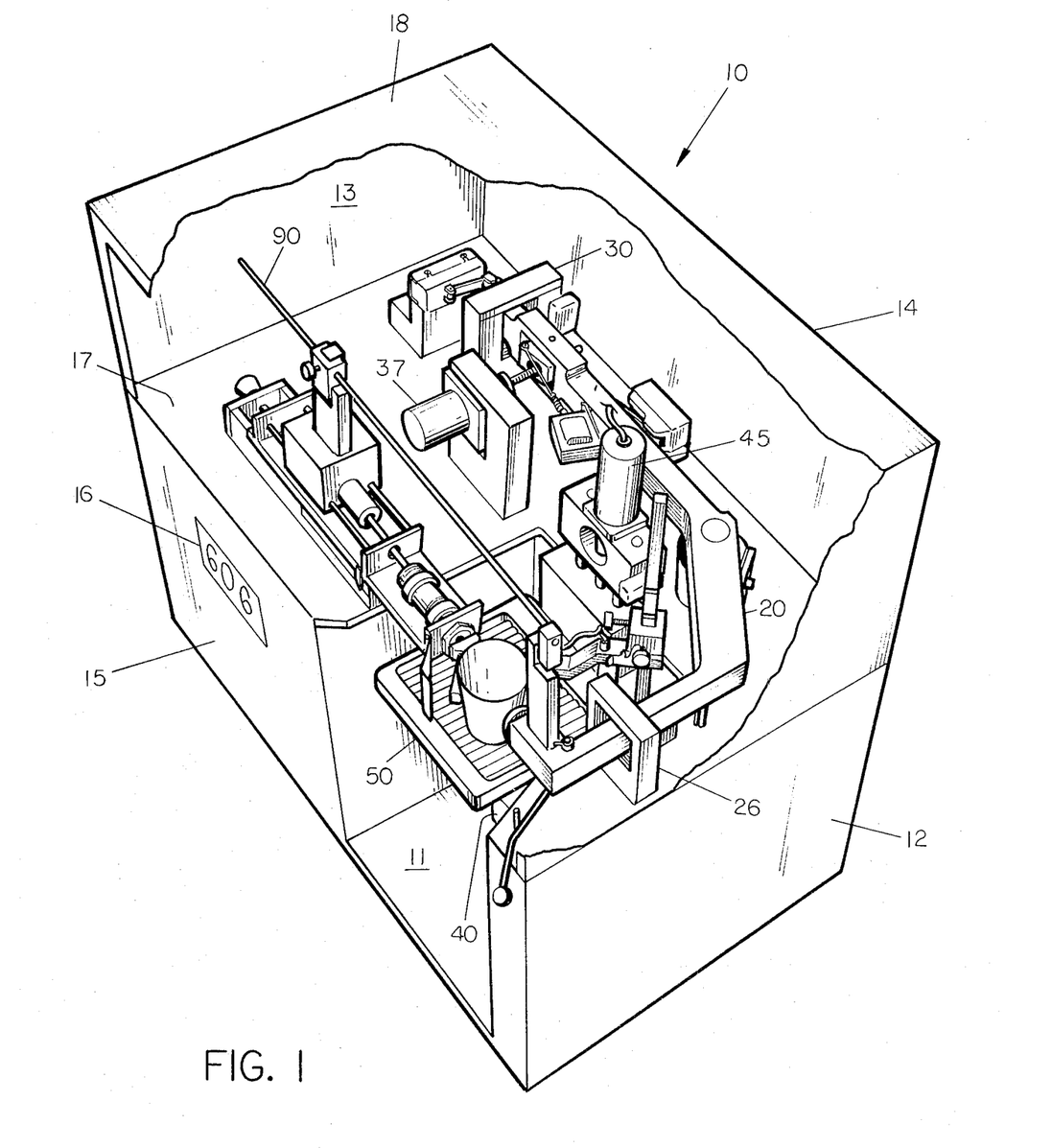
FIG. 1 is a perspective view showing the overall apparatus with part in section.

The overall container testing apparatus is shown in FIG. 1 at 10. The overall apparatus 10 is of cubic configuration and consists of a base 11 for resting on any relatively flat surface such as for example a laboratory bench. The overall apparatus 10 has sides 12 and 13 attached to base 11 and oriented in a vertical direction. A back structure 14 is attached to base 11 and sides 12 and 13. Panel 15 faces the front and provides a working surface for the mounting of digital panel meter 16 and various control switches which will be commented upon later.

A support deck 17 is mounted approximately halfway between base 11 and top 18. The support deck contains the majority of the moving parts associated with the overall apparatus 10.

Figure 2:
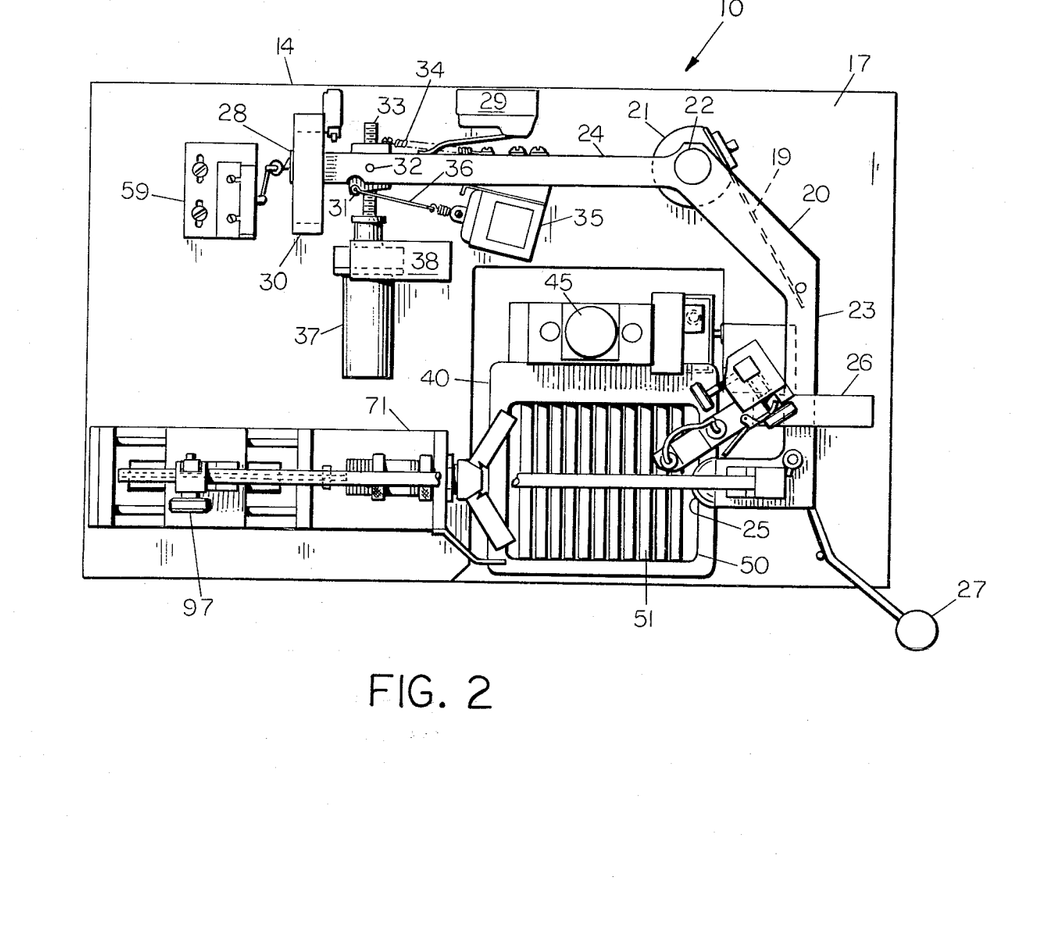
FIG. 2 is a plan view that shows the upper structural parts of the apparatus.

Referring now to FIG. 2, a force arm assembly 20 is mounted for pivotal movement about a support pedestal 21 that contains an upright mounting pin 22. The support pedestal 21 is anchored to the top of support deck 17. The force arm assembly 20 has a limited degree of freedom for angular movement about mounting pin 22. Force arm assembly 20 is divided into two arms, a forward arm 23 and a rear arm 24. The forward arm 23 terminates at its free end with a force button 25. The force button 25 is hemispherical in configuration and is used to contact the rim or surface area of the container as will be more fully explained later. The forward force arm 23 passes through a force arm guide 26 which permits relatively free horizontal movement while providing a moderate degree of movement restriction in a vertical direction. A handle 27 is cantilevered from the forward force arm 23, thus providing easy accessibility to the force arm assembly 20 for manual movement as the occasion demands through the test routine. The rear force arm 24 extends along and is generally parallel to the back structure 14 of the overall apparatus 10. The free end 28 of rear force arm 24 passes through and is supported by force arm guide 30. Force arm guide 30 operates in a manner similar to force arm guide 26 which was previously described. Rear force arm 24 carries a clutch nut 31, also known as a quick acting swivel nut, within the arm structure and located toward the free end 28. Clutch nut 31 is contained within a transverse slot in rear force arm 24 and is pivoted about pivot point 32. The clutch nut 31 contains a bore through it and has threaded segments therein. When the clutch nut 31 is aligned perpendicular to the longitudinal axis of rear force arm 24, the threaded segments are in a position to engage a threaded rod 33. When the clutch nut 31 is rotated clockwise, the threaded segments become disengaged with the threaded rod 33. A tension spring 34 is attached to one side of clutch nut 31. The other end of tension spring 34 is attached to the side of rear force arm 24. Thus, acting under the biasing action of tension spring 34, the clutch nut 31 is kept in the open or disengaged position. So long as clutch nut 31 is in the disengaged position, the rear force arm 24 is free to rotate about the mounting pin 22. A clutch solenoid 35 is attached to the rear force arm 24 intermediate the position of nut 31 and support pedestal 21. The movable core of clutch solenoid 35 is attached to a tension bar 36. Tension bar 36 is also attached to one side of clutch nut 31. This attachment is opposite to the side where tension spring 34 is attached. When clutch solenoid 35 is activated, tension bar 36 will be pulled toward the solenoid, consequently, the clutch nut 31 will be rotated in a clockwise direction about pivot point 32, thus locking the threaded segments into engagement with the threaded rod 33.

The threaded rod 33 is an extension of the axially aligned shaft of force motor 37. Force motor 37 is held in position by force motor mount 38 which is mounted in an upright fashion from support deck 17.

Thus it can be ascertained when clutch solenoid 35 is activated, clutch nut 31 will engage the threads on threaded rod 33. When threaded rod 33 is rotated by force motor 37, the entire force arm assembly 20 will rotate about mounting pin 22.

Figure 3:
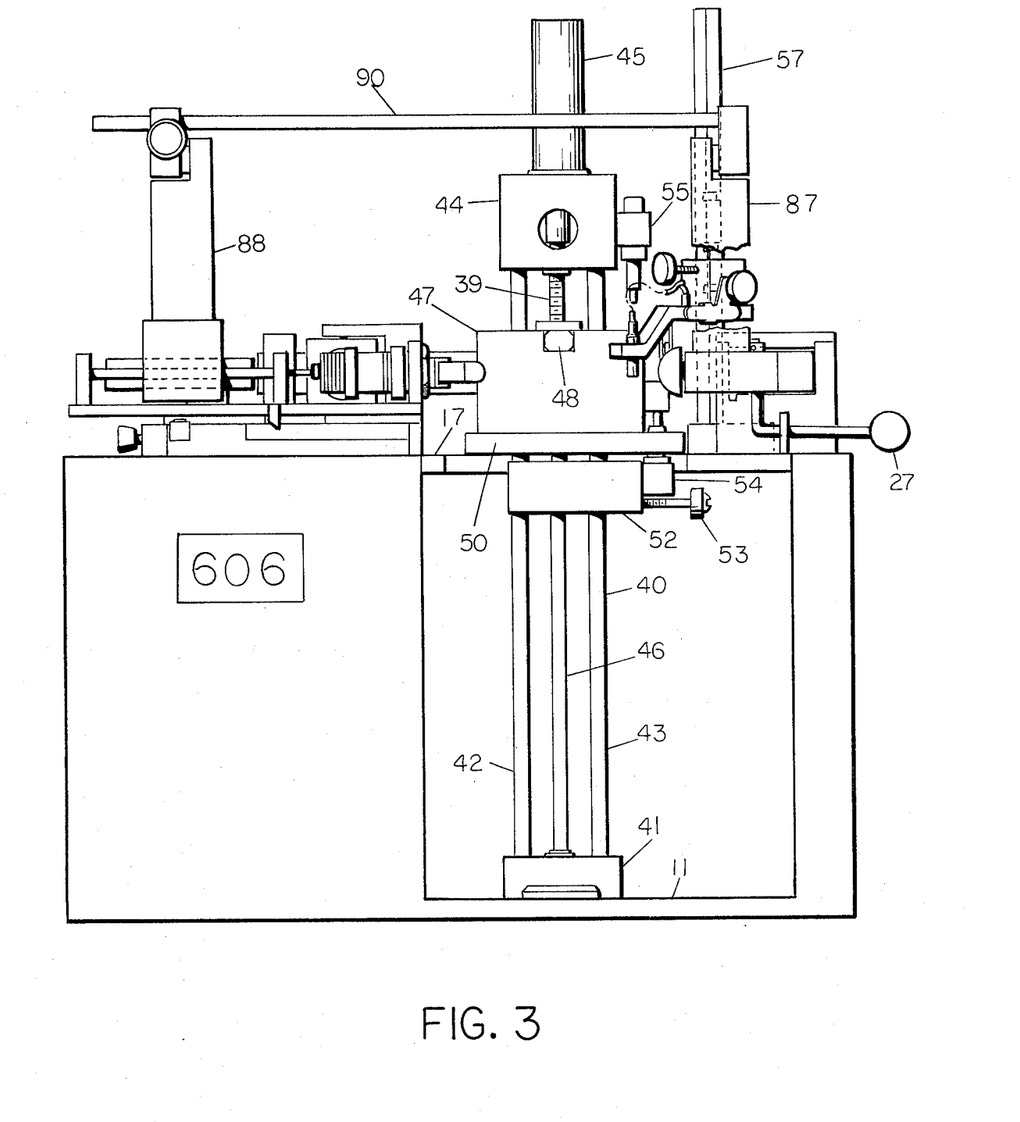
FIG. 3 is a front elevational view that shows the elevator mechanism.

Referring once again to FIG. 1, an elevator assembly 40 can be seen in the lower section of overall apparatus 10. The elevator assembly 40 can also be seen in FIG. 2, as well as FIGS. 3 and 4. The elevator pedestal 41, as shown in FIG. 3, is attached to base 11. Vertically oriented support rods 42 and 43 are rigidly attached to elevator pedestal 41. The upper ends of support rods 42 and 43 terminate with and are held by motor support block 44. A high torque elevator motor 45 is attached to the top of motor support block 44. The longitudinal axis of motor 45 is aligned in the vertical direction and is positioned equidistant between support rods 42 and 43. The shaft (not shown) of motor 45 points vertically downward and is directly coupled to drive shaft 46 which is positioned between and parallel to support rods 42 and 43. Drive shaft 46 is journaled for rotational movement at its lower end which terminates in elevator pedestal 41. A rather low angle pitch thread 39 extends the entire length of drive shaft 46.

An elevator slide block 47 is mounted for vertical up and down movement on support rods 42 and 43. An internally threaded nut 48 is attached to elevator slide block 47 as shown in FIG. 3. Internally threaded nut 48 is in threaded engagement with drive shaft 46. Thus, when drive shaft 46 rotates, nut 48 will travel in an up or down direction since it is fixed against rotation. Since nut 48 is attached to elevator slide block 47, it also will move up and down as drive shaft 46 undergoes rotation under the influence of motor 45.

Figure 4:
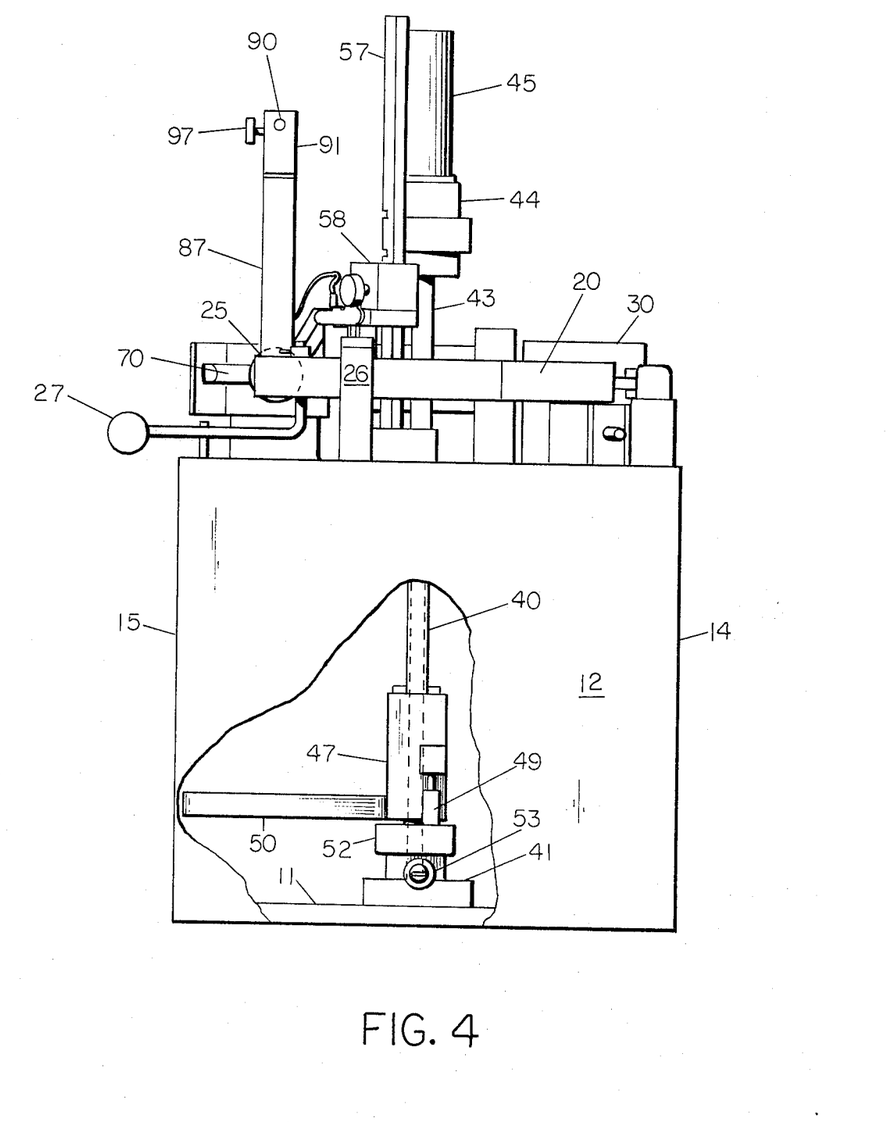
FIG. 4 is a side view that also shows the elevator mechanism.

Referring to FIG. 4, it can be seen that elevator slide block 47 has a cantilevered elevator platform 50. Elevator platform 50 is also clearly shown in FIG. 2. The deck or flat expanse of the elevator platform 50 is comprised of a series of parallel oriented container support rods 51 as best seen in FIG. 2. The support rods 51 are supported in bearings that are mounted in the framework of elevator platform 50 and are each free to rotate. Thus it can be realized that if an object such as a container is placed upon the support rods 51, it can easily moved from right to left as viewed in FIG. 2.

Situated immediately below elevator slide block 47 is an auxiliary slide block 52. Slide block 52 also is free to travel up and down along the vertical extent of support rods 42 and 43. Slide block 52 can be positioned manually at any position by loosening hand screw 53, then retightening it after a new position for auxiliary slide block 52 has been selected. A limit switch 54 is attached to auxiliary slide block 52 and is oriented in an upward direction. The limit switch 54 sets the lower limit of travel of elevator slide block 47.

Referring now to motor support block 44, an additional limit switch 55 is positioned in a downward direction. This limit switch 55 limits the upward travel of elevator slide block 47.

Figure 5:
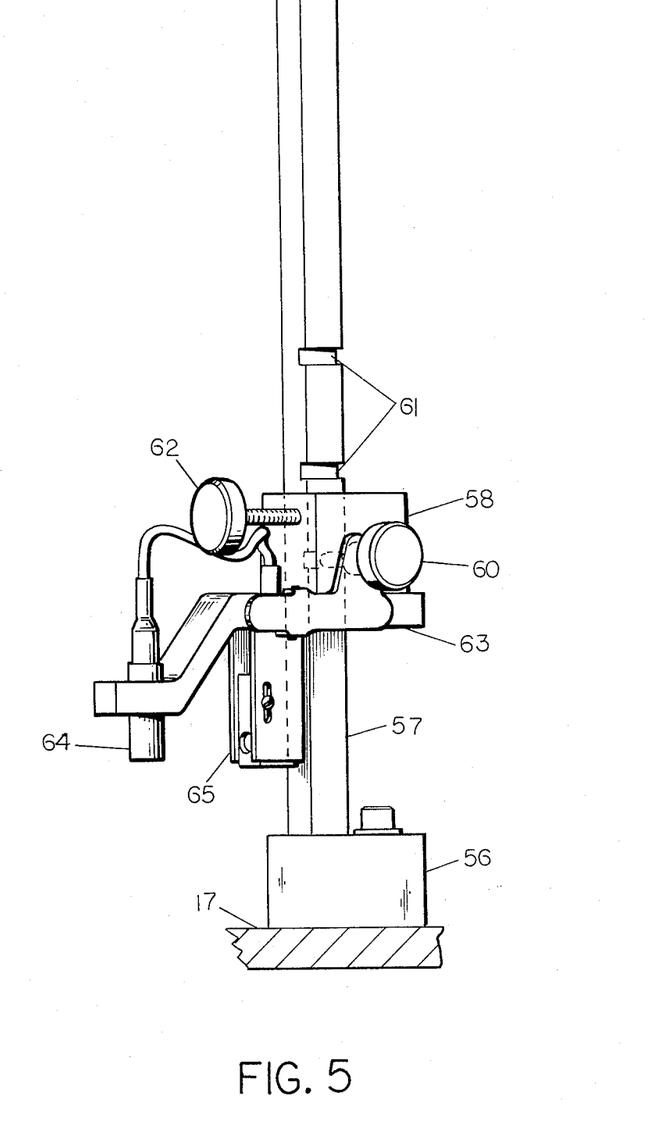
FIG. 5 is a view of the photoelectric cell and its associated receptor unit.

FIG. 5 is also related to the upward travel of elevator slide block 47. FIG. 5 shows a support block 56 that is attached to the top surface support deck 17 of overall apparatus 10. An upright column 57 is cantilevered in a vertical direction from support block 56. A slide 58 is fixed to column 57 so that it has one degree of movement, that is, up and down along column 57. A spring loaded detent 60 is mounted in and through slide 58. The inner end of detent 60 engages one of the milled notches 61 in column 57. Thus, by merely applying an outward force to detent 60, the slide 58 can be positioned at any one of the desired elevations defined by notches 61. The slide block 58 can also be set at elevations intermediate of notches 61 by the utilization of clamp screw 62. The slide block 58 can also be positioned at any elevation by first pulling out detent 60, then repositioning slide 58 to the desired location at any position along column 57, then clamping clamp screw 62 against the surface of column 57. At the same time, detent 60 is merely sliding along the surface of column 57.

A generally horizontal bar 63 is coupled to slide 58. A photoelectric receiving cell 64 is attached to the extremity of the bar 63 and a photoelectric sending or light source 65 is attached to bar 63 at a position remote from the end of the bar 63. As can be seen from FIG. 5, there is a short space between receiving cell 64 and sending source 65.

In the operation of the just described photoelectric sending-receiving unit, it is positioned so that the rim of a container will enter the space between receiving cell 64 and sending source 65. The container rides on the elevator platform 50, thus the container is lifted until its rim passes through the light beam of sending source 65. The electrical signal produced by the cutting of the light beam stops the upward movement of the elevator.

Figure 6:
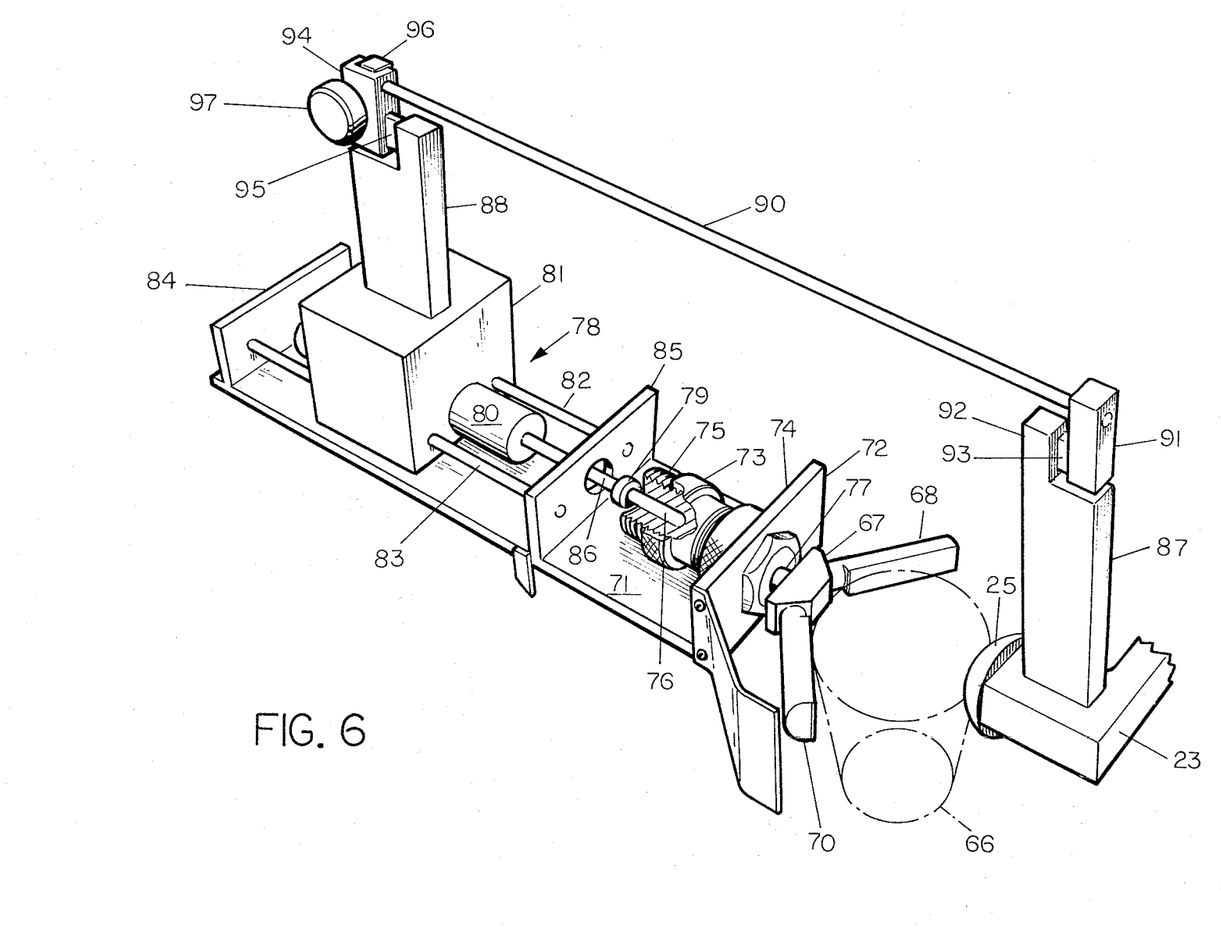
FIG. 6 is a perspective view that shows, part in section, the force and deflection measuring system.

FIG. 6 is a perspective view of the force recording mechanism of the present invention. The forward arm 23 of force arm 20 is shown at the right hand side of FIG. 6. Likewise, the force button 25 is shown as it is attached to the end of forward arm 23. A container, such as for example a cup, is shown in phantom at 66. The container 66 is grasped by force button 25 on one side and by the support anvil assembly 67 on the other side. The support anvil 67 is bifurcated and contains outstanding arms 68 and 70 which will be commented upon in more detail later.

The support anvil assembly 67 is supported generally by base 71 as shown in FIG. 6. Base 71 is movably attached to the support deck 17 of apparatus 10 by a structure that permits adjustments to be made. The base 71 has an upstanding leg 72 that is fixed thereto in perpendicular fashion. A force cell assembly 73 is mounted in cantilevered suspension from the inboard side 74 of upstanding leg 72. The force cell assembly 73 is comprised of an outer coil arrangement 75 and a movable core element 76. The coil 75 and the movable core element 76 provide an electrical means for determining how much linear movement the core element 76 has undergone. The core element 76 passes freely through an aperture 77 in upstanding leg 72 and terminates with its end firmly attached to the support anvil 67.

Positioned to the left of the force cell assembly 73 and as shown also in FIG. 6, is a linear variable displacement transducer (LVDT) assembly 78. The coil 80 of the LVDT assembly 78 is immobilized in and with mounting block 81. The mounting block 81 is in turn supported by rods 82 and 83 which permit the mounting block 81 to move freely from left to right as shown in FIG. 6. The support rods 82 and 83 are rigidly fixed at their ends to support blocks 84 and 85.

The LVDT core 86 is suspended freely within its companion coil 80 and is attached to the movable core 76 of the force cell assembly 73 by a coupling device as shown at 79. Thus it can be observed that the support anvil 67, the force cell core 76 and the LVDT coil 86 are all connected rigidly together.

Attention is now directed to the forward arm 23 as shown in FIG. 6. A post 87 is fixed in a rigid manner to forward arm 23. A similar upright post 88 is rigidly mounted to the top of mounting block 81 which is shown in the left hand side of FIG. 6. An interconnecting adjustment rod 90 spans the distance between upright posts 87 and 88. An attachment bar 91 is fixed to the right hand end of adjustment rod 90. The attachment bar 91 is coupled to the top section 92 of post 87 by a flexible member 93. The flexible member 93 bends easily in the lateral direction, however, it is rigid enough to resist deflection in an axial direction or in the direction assumed by adjustment rod 90. A movable attachment bar 94 is coupled to post 88 by flexible member 95. The movable attachment bar 94 contains a clamp member 96 that is held in position by means of clamp screw 97. When clamp screw 97 is in the loose position, adjustment rod 90 can move freely between attachment bar 94 and clamp member 96. Thus it can be observed the free span of adjustment rod 90 can be shortened or lengthened as desired.

When the clamp screw 97 is in the tightened position, the attachment bars 91 and 94 will move with adjustment rod 90 as a unit. Likewise, posts 87 and 88 will move in unison. The flexible members 93 and 95 permit slight rotary motion to occur since the forward arm 23 of force arm 20 is not moving entirely in the direction assumed by adjustment rod 90. Force arm 20 is actually rotating about mounting pin 22 as previously set forth.

During the test procedure which will be described fully hereinafter, any initial movement, such as for example a preload condition, will cause a corresponding movement of movable core 76 of force cell assembly 73. At the same time core 76 is undergoing movement, the LVDT core 86 is also undergoing the same movement since both cores 76 and 86 are directly coupled together. The coil 80 of the LVDT is also permitted to move because it is coupled to the movement of forward arm 23, thus both the coil, as well as the core of the LVDT, can move. In this manner the movement caused by the force cell assembly core 76 is compensated for.

To better explain the above operation and interaction of the force cell assembly 73 and the LVDT assembly 78, assume that the force cell assembly 73 contains a biasing means in the form of a spring (not shown) that reacts the load delivered to the container 66 by force button 25. The biasing spring is connected to the movable core 76 and the outer housing of the force cell assembly 73 which in turn is rigidly connected to the upstanding leg 72 of base 71. Thus, the thrust or force by container 66 against support anvil 67 is reacted by the internally positioned spring means within the force cell assembly 73. As previously stated, the movable core 76 of the force cell assembly 73 and the LVDT core 86 are rigidly connected to one another. In order for the force cell assembly 73 to function, it must undergo a certain deflection, for example, 0.20 inch. This deflection is the direct result of force button 25 pushing against container 66 which in turn pushes against support anvil 67. The LDVT core 86 also moves the same 0.20 inch because it is directly coupled to the force cell assembly core 76. At the same time the LDVT coil 80 is also moving 0.20 inch since the LDVT coil 80 is movable and connected to the force arm 20 by means of adjustment rod 90. The net result or differential movement between the LVDT core 86 and coil 80 is zero. When, during a test procedure, container 66 deflects because of the applied load of force button 25, there will be a differential movement between the LVDT core 86 and coil 80. Any movement attributable to the force cell assembly 76 will be compensated for and not recognized by the LVDT. The relative movement between the LVDT core 86 and coil 80 is the true deflection of the container 66.

Figure 7:
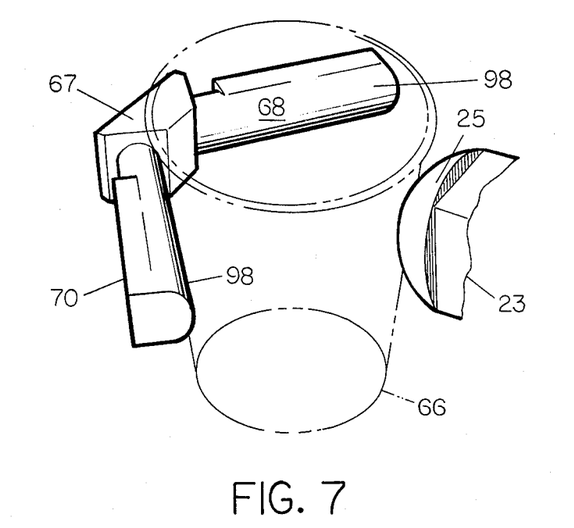
FIG. 7 is a perspective view of a container as it is grasped by the sidewall.

FIG. 7 is an enlarged perspective view of container 66 with force button 25 resting against one side of the container and the support anvil assembly 67 positioned against the opposite side of the container 66. The bight afforded by arms 68 and 70 of anvil assembly 67 provide a self-centering feature which assures that similar containers will be grasped in identical fashion. Referring particularly to the free end of arm 70, it can be observed the contact edge 98 is rounded, yet provides adequate line contact for the support of container 66.

Figure 8:
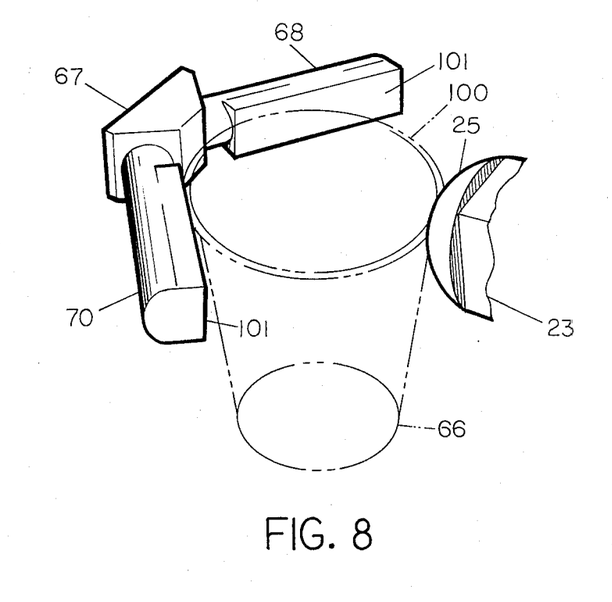
FIG. 8 is a perspective view similar to FIG. 7 except that the container is grasped by the rim.

While keeping in mind the arrangement just described in association with FIG. 7, reference is made to FIG. 8. It will be noted that the containers 66 is mounted so that the load is being applied to the rim 100 of the container rather than to the container sidewall. FIG. 8 shows that the arms 68 and 70 have been rotated 180 degrees, thus permitting the flat area 101 of arms 68 and 70 to bear against the container rim 100. The flat areas 101 provide a better support for the container rim than does the more rounded side 98 described in the description of FIG. 7. The position of arms 68 and 70 is moved quickly from flat side contact to round side contact with the container by simply rotating the arms. A simple detent means (not shown) permits the arms to be fixed in either one of the desired test positions.

Figure 9:
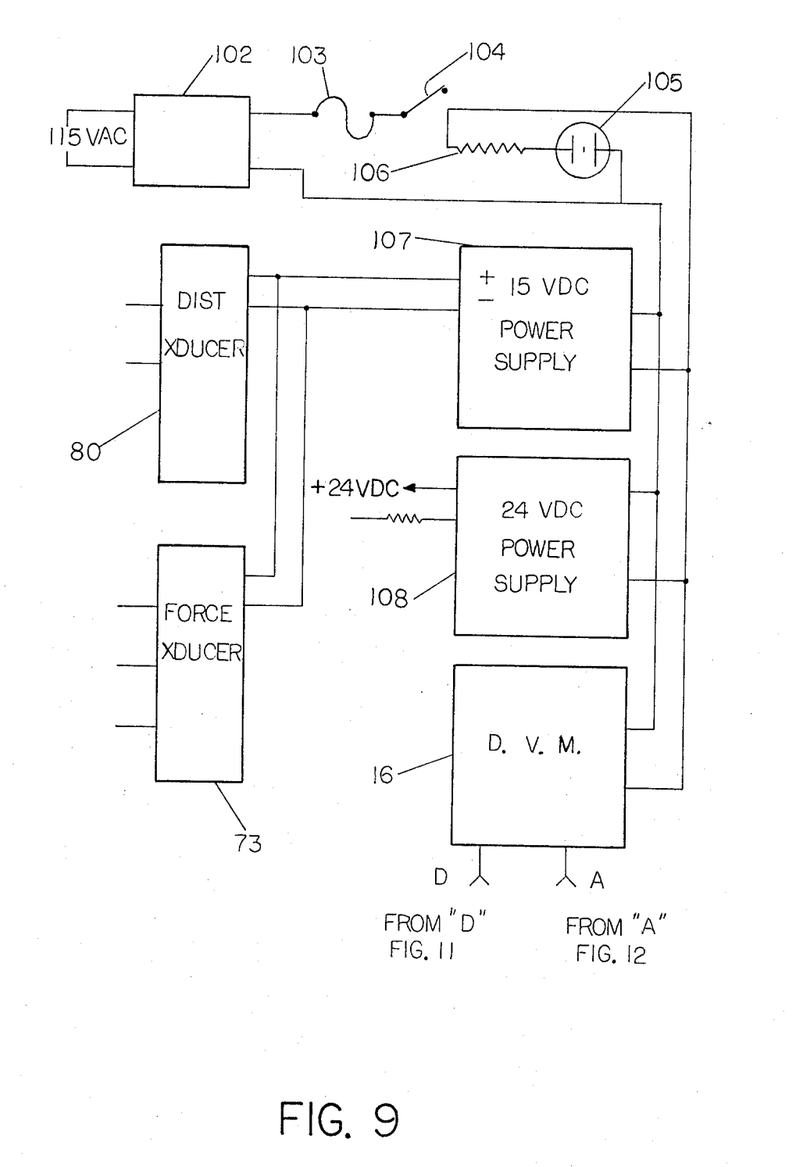
FIG. 9 is a schematic showing the power supply and line filter.

FIG. 9 is an electrical schematic drawing which shows typical 60 cycle 115 volt alternating current being applied to line filter 102. One of the incoming lines is fused as shown at 103. A power on-off switch 104 is positioned in the line that carries fuse 103. A power on light 105 is connected in series with switch 104 through a current limiting resistor 106 since line current would be detrimental to light 105. Through a series of parallel coupling, the line voltage is applied to a plus or minus 15 volt direct current power supply 107 which serves as a power source to the analog power board and subsequent electronic circuits. The line voltage is also supplied to a 24 volt direct current power supply 108 which supplies power to the force motor 37 and the elevator motor 45.

The plus or minus 15 direct current voltage coming from analog power supply 107 and as shown in FIG. 9 is delivered to the LVDT assembly 80 and through a parallel connection to the force cell assembly 73.

Figure 10:
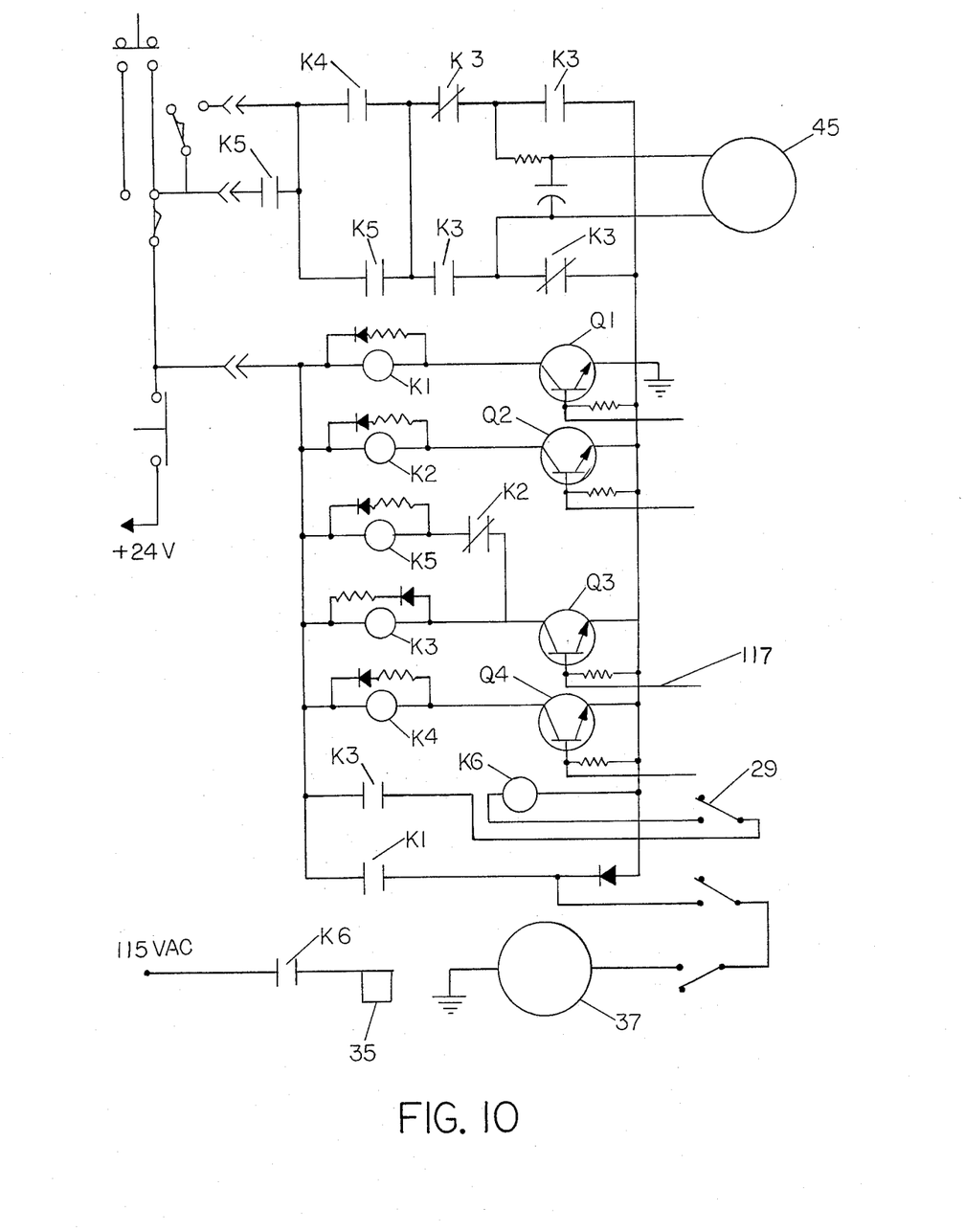
FIG. 10 is a schematic showing the primary relay system used with the present invention.

FIG. 10 shows an electrical diagram for the primary relay system employed by the present invention. The NPN transistors Q1, Q2, Q3 and Q4 are shown in association with their respective relays K1, K2, K3, K4, K5 and K6. The elevator motor is shown and represented by numeral 45 in the upper right hand portion of the figure. The force motor represented by numeral 37 is shown at the bottom of FIG. 10.

Also shown, at the bottom left of FIG. 10, is a diagram showing the interaction of K6 with the clutch solenoid 35.

Figure 11:
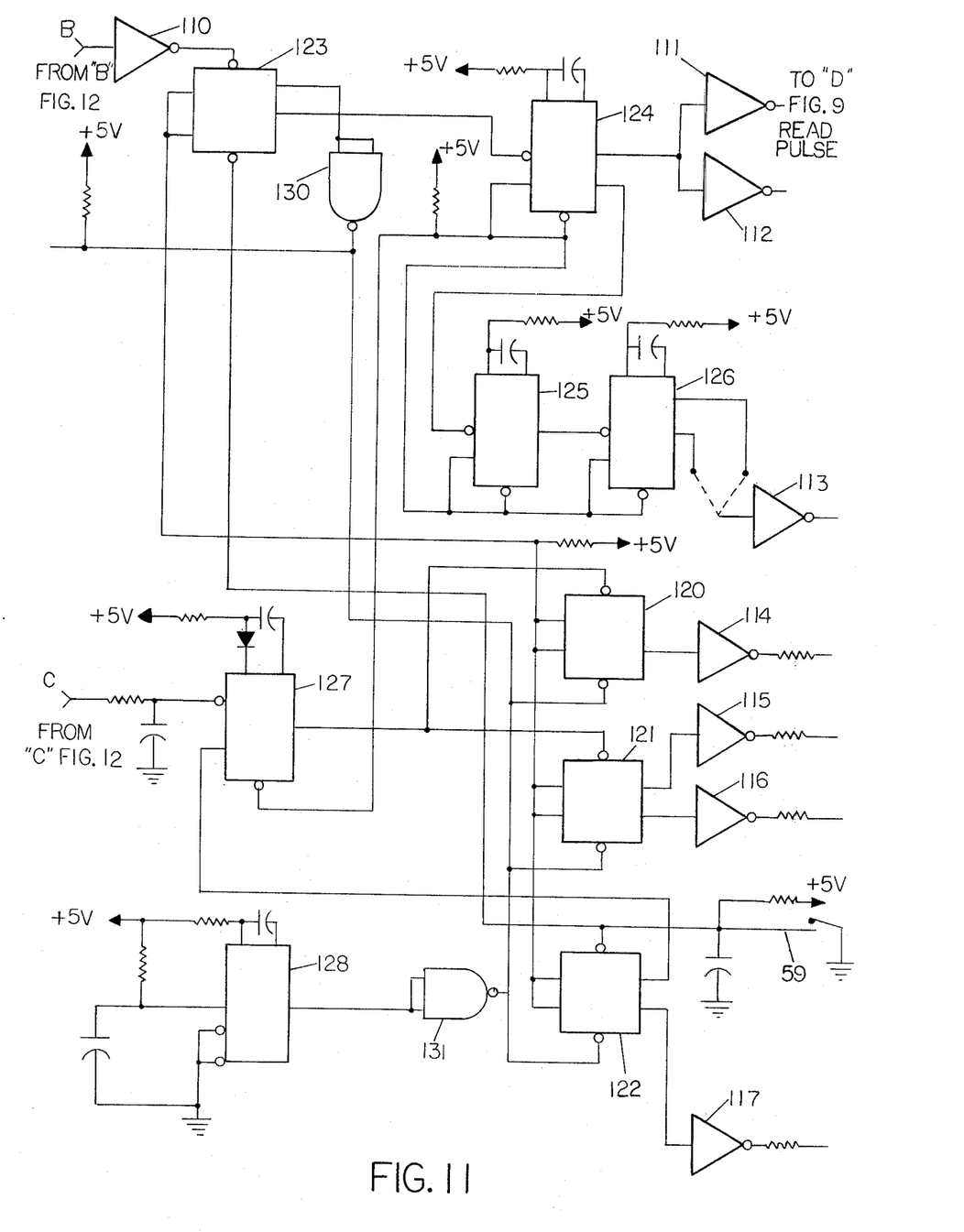
FIG. 11 shows the overall schematic for the digital logic circuits.

FIG. 11 depicts the digital logic circuit of the present invention. A series of inverters 110 through 117 are shown on FIG. 11. Also shown are flip-flops 120 through 123. A series of one-shot multi-vibrators are identified by numerals 124 through 128.

Figure 12:
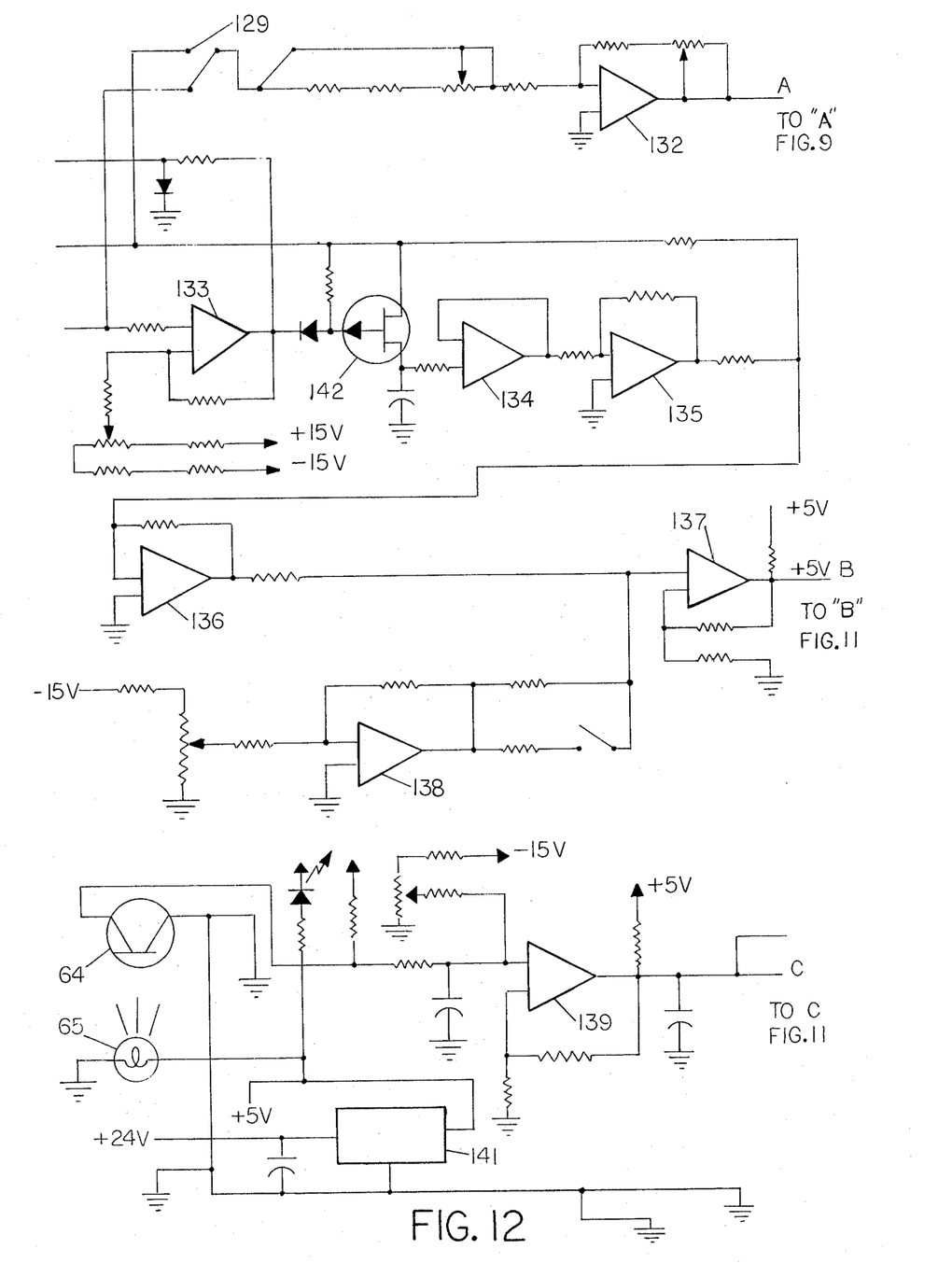
FIG. 12 shows the schematic for the analog control for the present invention.

FIG. 12 is an electrical diagram which represents the analog control for the present invention. Operational amplifiers 132 through 139 receive the incoming signals from the LVDT assembly coil 80 and the force cell assembly 73. A field effect transistor is identified by numeral 142 and a voltage regulator 141 is relied on to reduce the 24 volts to 5 volts for feeding the logic system.

For a more complete understanding of how the present invention operates, the following explanation is provided. At the beginning of the test sequence, elevator platform 50 is in the down position and force arm 20 is rotated, by a leaf spring attached to support pedestal 21, to the extreme counterclockwise position, thus placing handle 27 to the right. A cup such as is commonly fabricated from paper or plastic is placed on elevator platform 50 and centered as well as possible on rollers 51. The sequential test procedure is started by manually moving handle 27 to the left, thus rotating force arm 20 clockwise. The rear arm 24 closes microswitch 59 which is shown on FIG. 2 and on digital schematic FIG. 11. The closing of switch 59 starts elevator motor 45 and the elevator begins to move in an upward direction. The elevator platform 50 continues to move upward until the edge of the cup passes through the space between receiving cell 64 and sending cell 65 of the photoelectric eye assembly shown in detail in FIG. 5. The breaking of the signal within the photoelectric eye causes elevator platform 50 to stop. The electrical sequence is as follows; as soon as microswitch 59 closes, flip-flop 122 changes state, thus causing the inverter 117 to turn on transistor Q3. Thus relay K5 becomes energized along with the turning on of Q3. Relay K3 also becomes energized when Q3 is turned on. Relay K3 reverses the polarity of the voltage to the elevator motor and K5 applies the voltage. With the elevator motor 45 in the presently described polarity, the elevator will rise. As soon as the cup edge progresses upward breaking the continuous signal flowing through the electric eye, operational amplifier 139 turns off. When amplifier 139 turns off, the multi-vibrator 127 fires, thus causing flip-flop 120 and 121 to change state from the state existing subsequent to initialization and prior to the commencing of the test. Flip-flop 120 through inverter amplifier 114 energizes K1 through Q1 on the relay diagram shown in FIG. 10. Since K1 is energized, power is supplied to force motor 37.

The moving of lever arm 27 to the left and the closing of microswitch 29 energizes clutch solenoid 35 through K6 on the relay board. At this time clutch nut 31 moves into firm engagement with threaded rod 33 which is an extension of the armature shaft of force motor 37. As a result of the operation of force motor 37, the entire force arm assembly 20 begins to rotate in a clockwise direction. The force button 25 then drives the cup toward and centers it in the bifurcated support anvil 67. Should perchance a cup not be in position, the elevator 40 will reach its upper limit and be stopped by limit switch 55. With a cup in place, the LVDT assembly 78 will be at some negative voltage when force button 25 impresses a force on the cup which is clamped between button 25 and anvil 67. A force potential is applied to operational amplifier 133 which switches off the field effect transistor 142 shown on the analog schematic of FIG. 12. A reference potential related to the LVDT assembly coil 80 voltage at that exact moment is fed to operational amplifier 134. Operational amplifier 135, which is connected to operational amplifier 134, inverts this potential. The voltage from LVDT coil 80 is combined with the voltage coming from operational amplifier 135 and is presented to the summing junction of operational amplifier 136. The applied voltage to operational amplifier 136 is presented to the input of comparator amplifier 137. A reference voltage is also supplied to operational amplifier 137 from operational amplifier 138. When the LVDT assembly coil 80 voltage reaches the comparator voltage which is applied to operational amplifier 137 from 138, 137 then changes state which results in an end of test signal at B FIG. 12. The end of test signal then progresses to the digital circuitry to flip-flop 123 shown at the top of the digital schematic of FIG. 11. Flip-flop 23 changes state and causes flip-flops 120, 121 and 122 to reverse their states. At this time flip-flop 123 triggers the one-shot multivibrator 124 to generate a trigger pulse at D FIG. 11 for the digital panel meter 16 to read the analog voltage presented to it provided by operational amplifier 132 as shown on the analog schematic point "A" of FIG. 12.

Since flip-flop 120 on the digital board has just changed state, the force motor 37 now stops. Flip-flop 121 sends a signal to the elevator down relay K4 through Q4. Relay K4 is thus energized. The elevator motor 45 is now reversed through flip-flops 121 and 122. The elevator now moves in a downward direction and when it reaches the down limit switch 49 as shown in FIG. 4, the power to the elevator motor 45 is disconnected and the elevator comes to rest in its downwardly most position.

The force voltage which the force transducer assembly 73 generates is applied to the operational amplifier 132 which interprets the force voltage into units of force which are displayed on the digital panel meter 16 as grams. The selective switch 129 shown at the top of FIG. 12 permits the digital panel meter to read in units of distance such as in thousands of an inch.

Relay K6 is ultimately turned off through the action of K3, as a result of this, the clutch nut 31 is disengaged from threaded rod 33 of force motor 37.

To return all units to a common starting point, an initialization is made through multi-vibrator 128 when the power is turned on. The initialization is as follows; after the initialization, the force motor 37 power is turned off through flip-flop 120 and K1. At the same time, the elevator down enabling relay K4 is turned on and the elevator up stop relay K2 is turned off. The elevator motor reversing relay K3 is likewise turned off. The elevator up start relay K5 is de-energized through the interconnecting contacts of K2 through Q3 which at this time is off. Relay K5 receives no power because Q3 is off.

As a result of the above described apparatus, it is therefore apparent that containers can be quickly and conveniently tested for their deflection characteristics. Moreover, the test results obtained at one test site can be correlated with similar tests conducted at another test site since there is little, if any, operator influence on the tests performed.

What is claimed is:

1. An apparatus for measuring the resiliency of an object, a movable force arm for applying a force against said object, a support anvil positioned so as to react to the force applied to the object by the force arm, a force cell having a movable core that is attached to said support anvil, a linear variable differential transformer having a coil with a movable core positioned therein, said force cell core attached to the linear variable differential transformer core and means connected between said force arm and the coil of the linear variable differential transformer so that the displacement of the force cell core does not influence the relative displacement between the core and coil of the linear variable differential transformer when a force is applied to said object, and means coupled to said force cell and said linear variable differential transformer to detect the magnitude of the force applied to the object after it has been permitted to deform a preselected amount.

2. An apparatus for measuring the resiliency of a container including a support deck, a force arm pivotably attached to said support deck, means coupled to one end of said force arm to cause it to rotate, force applying means attached to the other end of said force arm to deliver a force against said container, a force cell with a movable core, the exterior of said force cell attached to said support deck, the core of said force cell attached to a support anvil positioned so as to react to the force applied to the container by said force applying means, a linear variable differential transformer having a coil and a core each mounted for movement independent of each other, said force cell core attached to the linear variable differential transformer core and means connected between said other end of said force arm and the coil of the linear variable differential transformer, so that said other end of said force arm and the coil of said linear differential transformer move substantially together in the same direction when a force is applied to said container, and means coupled to said force cell and said linear variable differential transformer to detect the magnitude of the force applied to the container after it has been permitted to deform a preselected amount.

3. An apparatus for measuring the resiliency of a container including a base with upright sidewalls attached thereto, a horizontally disposed support deck attached to said sidewalls, a container support means disposed intermediate said base and said support deck, a force arm pivotably attached to said support deck, means coupled to one end of said force arm to cause it to rotate, the other end of said force arm positioned adjacent a first side of said container support means, a force applying means attached to said other end of said force arm to deliver a force against said container, a force cell attached to said support deck, said force cell having a movable core with one end attached to a support anvil that is positioned adjacent to and opposite the first side of said container support means, a linear variable differential transformer having a coil and a core each mounted for movement independent of the other, said linear variable differential transformer coil mounted on slide means attached to said support deck, said force cell core attached to the linear variable differential transformer core so that said cores move in unison, a rigid bar attached to said other end of said force arm and attached to the movable coil of the linear variable differential transformer, so that said other end of said force arm and the coil of said linear differential transformer move substantially in unison in the same direction when a force is applied to said container and means coupled to said force cell and said linear variable differential transformer to detect the magnitude of the force applied to the container after the container has been permitted to deform a preselected amount.

4. An apparatus for measuring the resiliency of a cup-like container including a base with upstanding sidewalls attached to it, a horizontally disposed support deck attached to and spanning the majority of the distance between said sidewalls, a container support elevator positioned to move up and down in the space between said base and deck, a force arm pivotably attached to said support deck and adapted to move in a horizontal direction, a drive motor mounted on said deck with drive means attached to one end of said force arm to cause it to rotate the arm about the pivot attachment, the other end of said force arm positioned adjacent a first side of said elevator, a force applying button attached to said other end of said force arm to deliver a force against a container which is supported on said elevator, a force cell the outer housing of which is attached to said support deck, said force cell having a movable core with one end attached to a bifurcated support anvil that is positioned adjacent to and opposite to the first side of said elevator, a linear variable differential transformer having a coil and a core each mounted for movement independent of the other, said linear variable differential transformer coil mounted on parallel slide bars which are attached to said support deck, said force cell core rigidly attached in linear fashion to the linear variable differential transformer core so that said cores move in unison, a vertically aligned cantilevered post attached to said other end of said force arm, a vertically aligned cantilevered post attached to the mvoable coil of the linear variable differential transformer, a rigid bar attached to said posts so that said other end of said force arm and the coil of said linear variable differential transformer move substantially in unison in the same direction when a force is applied to said container and electrical means coupled to said force cell and said linear variable differential transformer to detect the magnitude of the force applied to the container after said container has been permitted to deform a preselected amount.

5. An apparatus for testing a resilient cup including a base with upstanding sidewalls attached to it, a deck for supporting test apparatus positioned at an elevation above said base, said deck spanning the majority of the distance between said sidewalls, a cup support elevator assembly attached to said base and deck with means for moving the elevator up and down, in the space between the said base and deck, a force arm pivoted towards its center and attached to said deck and adapted for movement in a horizontal direction, a drive motor mounted on said deck, a drive screw attached to said motor and coacting with a quick-acting swivel nut located within and near one end of said force arm to cause it to rotate the arm about the pivot attachment, the other end of said force arm positioned adjacent a first side of said elevator, a force applying button attached to said other end of said force arm to deliver a force against a cup which is supported on said elevator, a force cell the outer housing of which is attached to said deck, said force cell having a movable core with one end attached to a bifurcated support anvil that is positioned adjacent to and opposite to the first side of said elevator, a linear variable differential transformer having a coil and a core each mounted for movement independent of the other, said linear variable differential transformer coil mounted on horizontally disposed parallel slide bars the ends of which are attached to said deck, said force cell core rigidly coupled in linear fashion to the linear variable differential transformer core so that said cores move in unison, a vertically aligned cantilevered post attached to said other end of said force arm and adjacent to said force applying button, a vertically aligned cantilevered post attached to the movable coil of the linear variable differential transformer, a rigid bar attached by flexture members to said posts so that the other end of said force arm and the coil or said linear variable differential transformer move substantially in unison in the same direction when a force is applied to said cup and electrical means coupled to said force cell and said linear variable differential transformer to detect the magnitude of the force applied to the cup after said cup has been permitted to deform a preselected amount.

6. A test apparatus as claimed in claim 5 wherein said elevator has a surface for supporting the cup comprised of cylindrical rollers.

7. A test apparatus as claimed in claim 5 wherein said elevator is raised and lowered by a motor driven screw threaded vertically mounted drive shaft.

8. A test apparatus as claimed in claim 5 wherein said bifurcated support anvil contains first and second support surfaces on each arm, said first surface being planar for coacting with the rim of a cup and said second surface being arcuate for coacting with the sidewall of a cup.

9. A test apparatus as claimed in claim 5 wherein one of said vertically aligned cantilevered posts contains an adjustment means so that the effective length of said rigid bar can be changed.

10. A test apparatus as claimed in claim 5 wherein a photoelectric sensing and receiving device is supported from said deck and is positioned so that the rim of a cup being tested can react therewith.

11. A test apparatus as claimed in claim 5 wherein said flexture members that are positioned at the ends of said rigid bar permit flexture in one direction while impeding flexture in a direction at right angles thereto.

12. A test apparatus as claimed in claim 5 wherein said quick-acting swivel nut is engaged and disengaged with said drive screw by the combination of a clutch solenoid and a tension spring.

13. A test apparatus as claimed in claim 5 wherein the core within the coil of the linear variable differential transformer is freely suspended without contacting the coil interior.

14. A test apparatus as claimed in claim 5 wherein the elevator assembly is mounted on a plurality of vertically aligned parallel bars which are attached to said base.

15. A test apparatus as claimed in claim 5 wherein said photoelectric sender and receiver can be adjusted to accommodate cups of different height.

16. The method of measuring the resiliency of a container including the steps of:
(a) positioning the container in an upright attitude, while supporting it by its base, so that a portion of the container remote from said base is positioned between a force generating arm and a force reacting anvil,
(b) applying a first small force normal to the axis of symmetry of said container to center the container between the force arm and the anvil,
(c) applying a second force in the same direction as said first force,
(d) reacting said first and second forces with a force cell attached to said anvil,
(e) measuring a preselected deflection of the container with a linear variable differential transformer that is directly coupled with said force cell,
(f) electrically determining the magnitude of the force applied to the container when said preselected deflection is attained.

17. The method of measuring the resiliency of a container including the steps of:
(a) positioning the container in an upright attitude, while supporting it by its base, so that the sidewall of the container is positioned between a hemispherically shaped force applying button and a bifurcated force reacting anvil,
(b) applying a first small force normal to the axis of symmetry of said container to center the container between the force applying button and the arms of the force anvil, (c) applying a second force in the same direction as said first force to the container sidewall, (d) reacting said first and second forces with a force cell core attached to said anvil, (e) measuring a preselected deflection of the container with a linear variable differential transformer the core of which is directly coupled with the force cell core and in which the coil of the linear variable differential transformer is directly coupled with the force applying button, (f) electrically determining the magnitude of the force applied to the container when said preselected deflection is attained.

18. The method set forth in claim 17 wherein the rim of the container set forth in step (a) is positioned between a hemispherically shaped force applying button and a bifurcated force reacting anvil.

19. The method of measuring the resiliency of a paper or plastic cup including the steps of:

(a) positioning the cup in an upright position on a cup support elevator while said elevator is in the down position, (b) moving said elevator to an up position so that the sidewall of the cup is positioned between a hemispherically shaped force applying button and a bifurcated force reacting anvil, (c) applying a first small force normal to the axis of symmetry of said cup center said cup between the force applying bottom and the arms of the force anvil, (d) applying a second force in the same direction as said first force to the cup sidewall, (e) reacting said first and second forces with a force cell core attached to said anvil, (f) measuring a preselected deflection of the cup with a linear variable differential transformer the core of which is directly coupled with the force cell core and in which the coil of the linear variable differential transformer is directly coupled with the force applying button, (g) electrically determining the magnitude of the force applied to the container when said preselected deflection is attained, (h) displaying visually the magnitude of said force.

20. The method set forth in claim 19 wherein the rim of the container set forth in step (b) is positioned between a hemispherically shaped force applying button and a bifurcated force reacting anvil.

* * * * *